US00PP36659P2

(12) United States Plant Patent
Kordes

(10) Patent No.: US PP36,659 P2
(45) Date of Patent: May 13, 2025

(54) MINIATURE ROSE PLANT NAMED 'KORpot135'

(50) Latin Name: *Rosa hybrida*
Varietal Denomination: KORpot135

(71) Applicant: W. KORDES' SÖHNE ROSENSCHULEN GMBH & CO KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/929,687

(22) Filed: Oct. 29, 2024

(30) Foreign Application Priority Data

Sep. 19, 2024 (QZ) ..... PBR 2247391

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121
See application file for complete search history.

(56) References Cited

U.S. PATENT DOCUMENTS

PP29,042 P3 3/2018 Kordes
PP36,042 P2 * 7/2024 Kordes ..... Plt./121

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot135', is described. The new variety forms in abundance on a substantially continuous basis, pink-colored blossoms. The growth habit is compact. Semi-glossy ornamental foliage is formed. Additionally, the new variety is particularly well suited for growing as distinctive ornamentation in the landscape.

1 Drawing Sheet

Latin name of genus and species of plant claimed: *Rosa hybrida.*
Variety denomination: 'KORpot135'.

CROSS REFERENCE TO RELATED APPLICATIONS

This application claims priority to Plant Breeders' Right Application No. 2247391, which was filed at Community Plant Variety Office in the European Union on Sep. 19, 2024, the contents of which are hereby incorporated by reference for all purposes.

STATEMENT REGARDING PRIOR DISCLOSURES BY THE INVENTOR

The first sale or offer for sale of the new variety was November 2023, on the Rosa Danica website (rosa-danica.dk). The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding during 2018, in Offenseth-Sparrieshoop, Germany by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) (not patented) of the new variety was a product of the cross between the 'RUId244a' variety (not patented) and a different unnamed breeder seedling (not patented).

The parentage of the new variety can be summarized as follows:

unnamed breeder seedling x ('RUId244a' x different unnamed breeder seedling)

The seeds resulting from the above pollination were sown and small plants were obtained which were physically and biologically different from each other. Selective study resulted in the identification of a single plant of the new variety.

The new variety has been found to undergo asexual propagation in Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms pink-colored blossoms, (b) provides double flowers with a rounded shape, and (c) exhibits a compact growth habit.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays a more rounded flower shape, and a smaller flower size compared to the unnamed breeder seedling parent (i.e., the seed parent). Additionally, the new variety displays a less intense pink flower color and a more compact growth habit compared to the pollen parent. Moreover, the new variety can be readily distinguished from non-parental related similar varieties. For example, the new variety displays a lower number of petaloids per flower and a more rounded flower shape compared to the 'KORpot064' variety (U.S. Plant Pat. No. 29,042).

The new variety has been named the 'KORpot135' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately sixteen weeks of age and was grown indoors on its own roots in a 10.5 cm container in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a three-year-old specimen of the new variety, observed during September 2024, while growing in a 7-gallon container on its own roots in a greenhouse in Cochranville, Pennsylvania.

Botanical classification: *Rosa hybrida* cultivar 'KORpot135'.

Commercial classification: Miniature Rose.

Plant:

*Habit*.—Compact.

*Height*.—Approximately 35.0 cm on average from the top of the soil plane when growing in a one-gallon container.

*Width*.—Approximately 33.0 cm on average.

Branches:

*Stem color*.—Young stems: Yellow-Green Group 144A.

*Length*.—Main stems: approximately 35.0 cm on average. — secondary stems: approximately 16.0 cm on average.

*Diameter*.—Main stems: approximately 8.0 mm on average. — secondary stems: approximately 3.0 mm on average.

*Texture*.—Glabrous.

*Prickles*.—Amount: very few. — young prickles: length is approximately 5.0 mm on average; width is approximately 4.0 mm on average at point of attachment; and color is Yellow-Green Group 144A. — old prickles: length is approximately 6.0 mm on average; width is approximately 5.0 mm on average at point of attachment; and color is Grey-Brown Group N199B.

Leaflets:

*Number*.—3, 5, and 7.

*Shape*.—Ovate; apex is acute; and base is rounded.

*Arrangement*.—Odd-pinnate.

*Margin*.—Serrate.

*Undulation*.—Weak.

*Glossiness of upper side*.—Semi-glossy.

*Texture*.—Upper surface: smooth. — under surface: smooth.

*Venation pattern*.—Reticulate.

*Size*.—Terminal leaflet: length is approximately 2.7 cm on average; width is approximately 2.0 cm on average. — lower leaflets: length is approximately 2.5 cm on average; width is approximately 1.6 cm on average. — 5-Leaflet leaf: length is approximately 7.0 cm on average; width is approximately 5.0 cm on average.

Foliage:

*Young foliage*.—Upper surface color: Green Group 143A with Yellow-Green Group 144B around edges with indistinguishable venation. — under surface color: Yellow-Green Group 146B with indistinguishable venation.

*Old foliage*.—Upper surface color: Green Group 137A with indistinguishable venation. — under surface color: Green Group 136B with Red-Purple Group 60A around edges with indistinguishable venation.

*Petiole*.—Texture: upper surface is mostly smooth with sparse prickles; under surface is mostly smooth with prickles. — length: approximately 1.0 cm on average. — width: approximately 1.0 mm on average. — upper surface color: Green Group 137A. — under surface color: Yellow-Green Group 144A.

*Rachis*.—Length: approximately 1.0 cm on average. — width: approximately 1.0 mm on average. — upper surface color: Green Group 137A. — under surface color: Yellow-Green Group 144A.

*Stipules*.—Length: approximately 9.0 mm on average. — width: approximately 2.0 mm on average. — margin: entire to erose. — upper surface color: Green Group 143C. — lower surface color: Green Group 138A.

Inflorescence:

*Number of flowers*.—About 35 to 40 blooms on average on a plant at once.

*Number of blossoms per stem or in a cluster*.—Typically 2 to 4 blooms per stem on average.

*Peduncle*.—Color: Green Group 143A. — diameter: approximately 1.0 mm on average. — length: approximately 2.5 cm on average. — surface texture: hispidulous.

*Sepals*.—Number: 5. — upper surface color and texture: Green Group 138B, covered in short pubescence. — under surface color and texture: Green Group 143A, puberulent. — size: length is approximately 2.6 cm on average; width is approximately 4.0 mm on average. — margin: entire with occasional extensions on two or three sepals measuring approximately 7.0 mm in length and 1.0 mm in width on average. — undulation: absent. — shape: lanceolate. — apex: acute to aristate. — base: truncate or flat as it joins the receptacle.

*Buds*.—Shape: rounded. — size: length is approximately 6.0 mm on average; width is approximately 1.0 cm on average. — color (when opening): Red-Purple Group 64D.

*Flower*.—Form: double, rosette. — profile: flat to slightly cupped. — diameter: approximately 4.5 cm on average. — height: approximately 2.0 cm on average. — duration: on the plant approximately 28 days. — petal color when first and fully opened: upper surface is Red-Purple Group 64D with a basal spot of Green- Yellow Group 1C; under surface is Red-Purple Group 63C with a basal spot of Green-Yellow Group 1C. — petal color at end of bloom: upper surface is Red-Purple Group 65D with a hint of Red-Purple Group 65B on the edges with a basal spot of Green-Yellow Group 1D; under surface is Red-Purple Group 65D with a hint of Red-Purple Group 65B on the edges with a basal spot of Green-Yellow Group 1D. — petals reflex one by one: yes.

*Fragrance*.—None noticeable.

*Petal*.—Number: 80 to 85 on average. — drop: average for the type. — length: inner petals are approximately 1.0 cm on average; outer petals are approximately 2.0 cm on average. — width: inner petals are approximately 6.0 mm on average; outer petals are approximately 1.6 cm on average. — overall shape: broadly obovate. — margin: entire. — apex shape: rounded. — base shape: rounded to cuneate. — texture: upper surface is glabrous; under surface is glabrous.

*Petaloids*.—Number: approximately 5 on average. — length: approximately 1.0 cm on average. — width: approximately 4.0 mm on average. — color: upper and under surfaces are Red-Purple Group 64D with a basal spot of Yellow Group 2B. — texture: smooth. — margin: variable; entire to erose. — shape: rounded and mostly curving inward. — apex: round. — base: cuneate.

*Stamen*.—Number: approximately 25. — anthers: number is approximately 25; color is Greyed-Orange Group 163A; length is approximately 1.0 mm on average; and shape is oval. — filaments: length is approximately 3.0 mm on average and color is Green-Yellow Group 1C.

*Pistils*.—Arrangement: separate and free. — number: approximately 35. — style: length is approximately 5.0 mm on average and color is White Group 155C. — stigma: diameter is less than 1.0 mm on average; shape is fan shaped; color is Greyed-Orange Group 163B.

*Receptacle*.—Diameter: approximately 4.0 mm on average. — shape: urn shaped. — color: Yellow-Green Group 144C. — surface texture: smooth.

*Pollen*.—None observed.

*Hips/seed*.—None observed.

Development:

*Vegetation*.—Medium green.

*Blossoming*.—Abundant and continuous; blooms may continue year-round if grown inside a warm greenhouse.

*Resistance to diseases*.—Good resistance for powdery mildew (*Sphaerotheca pannosa*) under normal greenhouse growing conditions in Cochranville, Pennsylvania.

*Hardiness*.—Unknown.

The new 'KORpot135' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot135' characterized by the following combination of characteristics:

(a) forms pink-colored blossoms, (b) provides double flowers with a rounded shape, and (c) exhibits a compact growth habit;

substantially as herein shown and described.

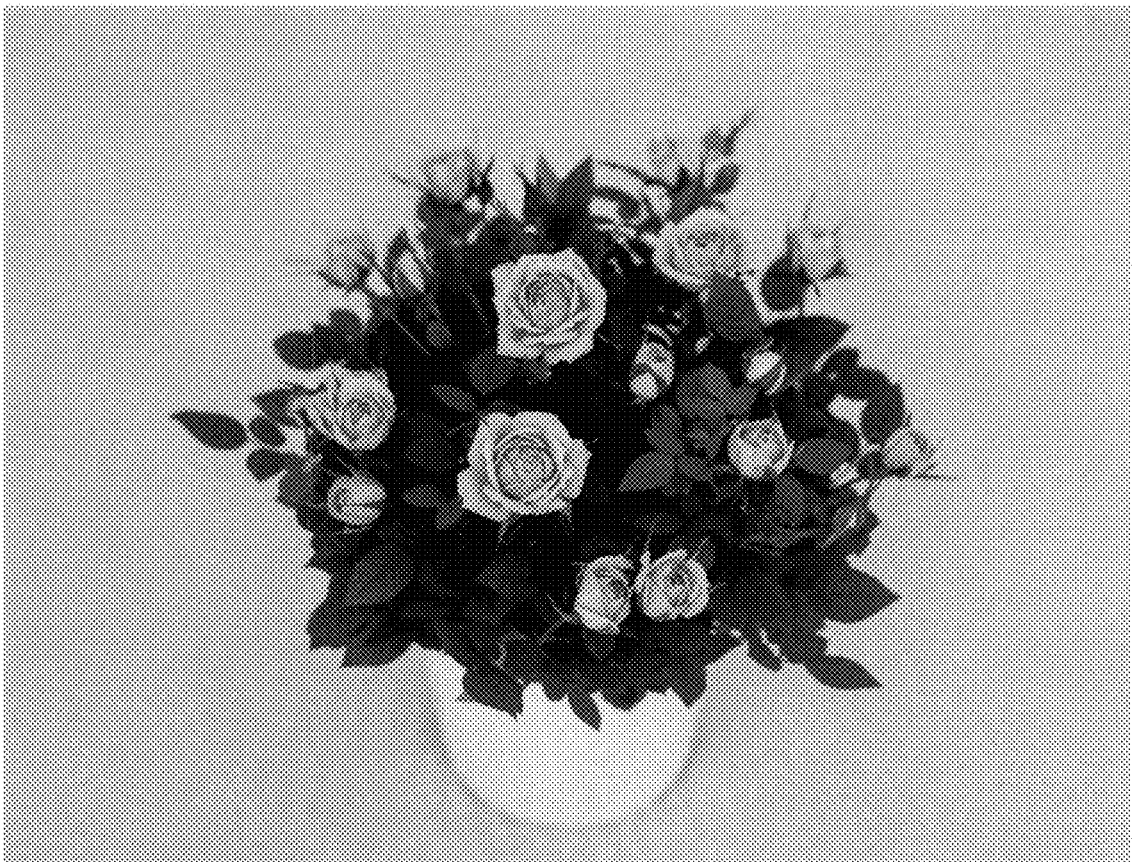

* * * * *